United States Patent
Vezzani

(10) Patent No.: US 11,185,816 B2
(45) Date of Patent: Nov. 30, 2021

(54) PROCESS AND PLANT FOR THE THERMAL ABATEMENT OF MALODOROUS EMISSION FROM A PURIFICATION PLANT WITH ENERGY RECOVERY FROM SAID ABATEMENT

(71) Applicant: Ambiente E Nutrizione S.R.L., Rozzano (IT)

(72) Inventor: Massimo Vezzani, Rozzano (IT)

(73) Assignee: Ambiente E Nutrizione S.R.L., Rozzano (IT)

( * ) Notice: Subject to any disclaimer, the term of this patent is extended or adjusted under 35 U.S.C. 154(b) by 249 days.

(21) Appl. No.: 16/344,514

(22) PCT Filed: Oct. 31, 2017

(86) PCT No.: PCT/EP2017/077909
§ 371 (c)(1),
(2) Date: Apr. 24, 2019

(87) PCT Pub. No.: WO2018/083097
PCT Pub. Date: May 11, 2018

(65) Prior Publication Data
US 2019/0291047 A1 Sep. 26, 2019

(30) Foreign Application Priority Data
Nov. 2, 2016 (IT) .......... 102016000110226

(51) Int. Cl.
| | | |
|---|---|---|
| *B01D 53/14* | (2006.01) | |
| *B01D 53/18* | (2006.01) | |
| *B01D 53/34* | (2006.01) | |
| *B01D 53/38* | (2006.01) | |
| *B01D 53/75* | (2006.01) | |
| *B01D 53/76* | (2006.01) | |
| *C02F 11/04* | (2006.01) | |
| *C02F 3/30* | (2006.01) | |
| *C12M 1/00* | (2006.01) | |
| *B01D 53/78* | (2006.01) | |
| *C02F 103/18* | (2006.01) | |

(52) U.S. Cl.
CPC ....... *B01D 53/343* (2013.01); *B01D 53/1425* (2013.01); *B01D 53/18* (2013.01); *B01D 53/38* (2013.01); *B01D 53/75* (2013.01); *B01D 53/76* (2013.01); *B01D 53/78* (2013.01); *C02F 3/302* (2013.01); *C02F 11/04* (2013.01); *C12M 43/04* (2013.01); *B01D 2252/103* (2013.01); *B01D 2257/90* (2013.01); *B01D 2258/02* (2013.01); *B01D 2258/05* (2013.01); *C02F 2103/18* (2013.01); *C02F 2209/02* (2013.01); *C02F 2303/02* (2013.01); *C02F 2303/10* (2013.01); *Y02W 10/30* (2015.05)

(58) Field of Classification Search
CPC ....... Y02E 50/30; Y02W 10/30; Y02W 10/20; B01D 2252/103; B01D 53/343; B01D 53/78; B01D 53/38; B01D 53/75; B01D 2258/02; B01D 2258/05; B01D 53/18; B01D 2257/90; B01D 53/76; C02F 2103/18; C02F 11/04; C02F 2303/02; C02F 3/302; C02F 2303/10
See application file for complete search history.

(56) References Cited

U.S. PATENT DOCUMENTS

| | | | |
|---|---|---|---|
| 4,857,458 A | 8/1989 | Nobilet et al. | |
| 7,604,743 B2 * | 10/2009 | Hirl ........... | C05F 5/008 210/603 |
| 8,157,993 B1 * | 4/2012 | Pedros ......... | C02F 3/302 210/188 |
| 2007/0102352 A1 * | 5/2007 | Burke ......... | C02F 3/06 210/603 |
| 2016/0250584 A1 * | 9/2016 | De Godos Crespo | C02F 11/04 95/92 |

FOREIGN PATENT DOCUMENTS

| | | |
|---|---|---|
| DE | 102010005253 A1 | 7/2011 |
| DE | 102012003246 A1 | 8/2013 |
| EP | 0646547 A2 | 4/1995 |
| FR | 2791339 A1 | 9/2000 |
| GB | 2509312 A | 7/2014 |
| JP | S61103598 A | 5/1986 |

OTHER PUBLICATIONS

Search Report and Written Opinion of PCT/EP2017/077909 dated Jan. 5, 2018.

* cited by examiner

*Primary Examiner* — Timothy C Vanoy
(74) *Attorney, Agent, or Firm* — Silvia Salvadori, P.C.; Silvia Salvadori

(57) ABSTRACT

A process and a plant for the thermal abatement of foul air containing malodorous substances. A flow of foul air containing malodorous substances as combustive air is fed into the combustion chamber of a unit for production and recovery of energy, and a flow of exhaust gas is obtained. The flow of exhaust gas is fed into a scrubber for the abatement of polluting substances, whereby the scrubber uses water for the washing of the flow of exhaust gas, producing a flow of low-temperature purified gas and a heated washing liquid. The heated washing liquid is conveyed to at least one heating jacket of a storage tank for the biological treatment of sewage of the aforementioned purification plant.

15 Claims, 3 Drawing Sheets

PROCESS AND PLANT FOR THE THERMAL ABATEMENT OF MALODOROUS EMISSION FROM A PURIFICATION PLANT WITH ENERGY RECOVERY FROM SAID ABATEMENT

This application is a U.S. national stage of PCT/EP2017/077909 filed on 31 Oct. 2017, which claims priority to and the benefit of Italian Patent Application No. 102016000110226 filed on 2 Nov. 2016, the contents of which are all incorporated herein by reference in their entireties.

FIELD OF APPLICATION

The present invention relates to a process for the thermal abatement of malodorous emissions from a purification plant with energy recovery from said abatement.

According to one aspect of the present invention, this process is applied to malodorous emissions from a plant for the treatment of urban or industrial waste waters and/or digestates. The invention also relates to a system for implementing the aforementioned process as well as to a method for revamping a conventional purification plant in order to make it suitable for implementing the aforementioned method.

PRIOR ART

It is well-known in the art that the disposal of waste waters from urban sewers and/or industrial discharge outlets, and the treatment of digestates, in both an industrial and an agricultural environment, are of fundamental importance in the context of sustainable urban development, from both an environmental and an economic point of view.

In particular, the waste waters must be necessarily subjected to a series of operations necessary for eliminating firstly the coarse material and the oily substances and then the organic matter dispersed therein.

More specifically, the waste waters are normally subjected firstly to preliminary treatment for eliminating coarse solids (screening), such as paper and plastic parts, and then the grit (degritting), followed by the oils and greases (oil and grease removal), which rise to the surface of the waters and would prevent the natural reoxygenation process.

Each system inside which one of the aforementioned preliminary treatment operations is performed operates simultaneously with an air recycling system which allows the foul air containing malodorous substances to be recovered and transferred to a deodorizing unit, normally included in a water treatment plant.

Thereafter, a series of operations which overall represent the biological treatment of the waters may be performed, these consisting essentially of two steps: a first de-nitrification step, during which the nitrites and the nitrates are converted into gasous nitrogen, and a second oxidation/nitrification step, during which the organic substance is converted into carbon dioxide in aerobic conditions by means of forced blowing of air and the ammonia (ammonium ions) is converted into nitrites and nitrates.

The aforementioned biological treatment steps are performed using active sludges containing mesophilic microorganisms at a temperature not higher than 45° C., typically comprised between 35° C. and 40° C.

This is followed by a sedimentation step during which the aerated mixture resulting from the oxidation/nitrification step is conveyed into settling tanks where the sludge produced settles by means of gravity; at the same time precipitation of the phosphates dissolved in the mixture is performed.

Finally, the effluent thus purified is subjected to a final finishing step (filtration) in order to eliminate the residual suspended particles; this may be followed by final disinfection, especially in the case where the water thus purified is transferred into an industrial aqueduct for reuse.

Optionally, often a line for treatment of the sludges from the biological treatment (de-nitrification, oxidation/nitrification) tanks and the settling tanks is arranged in parallel with the water line.

At the same time, purification plants with associated lines for treatment of the sludges from the various process steps are commonly present in large-size industrial plants.

In contexts such as those mentioned above, the sludges undergo firstly a pre-thickening step during which their density is increased by means of settling and elimination of resultant water; the latter may be transferred upstream of the purifier.

Each system within which the aforementioned pre-thickening step is carried out operates simultaneously with an air recycling system, which allows the foul air containing malodorous substances to be recovered and transferred to a deodorizing unit.

The sludges thus thickened may undergo an anaerobic digestion step, at a temperature typically comprised between 37° C. and 45° C. for a period of about 15 to 20 days, inside digesters with the production of any biogas, 65-70% of which consists of methane and the remainder of carbon dioxide and secondary by-products.

While the biogas thus produced may be sent to a motor generator unit for the production of electrical energy or to a boiler, the digestate, namely the residual sludges from digestion undergo further treatment, including a dehydration step, in order to obtain a dehydrated sludge.

Finally, the dehydrated sludge may be recovered for agricultural use or may be subject to a drying step inside a drier, often kept heated (200-220° C.) by a hot diathermic fluid, which may in turn be heated inside a boiler, for example the aforementioned biogas boiler or a conventional methane gas boiler.

At the output of the drier a line for the vapour condensate and a line for recovery of the dried sludge which may be used as fuel in power stations or foundries is provided. On the one hand, it is therefore clear how a process for the treatment of waters and/or digestates must comprise a deodorizing step for destruction of the malodorous substances contained in the recycling air which is produced during the various stages of the process (preliminary treatment and various operations along the sludge recovery line).

Generally, deodorization of the malodorous emissions from a waste water and/or digestate purification plant is performed by means of sequential washing of the air with chemical substances, generally carried out in a scrubber.

This air deodorization technique involves however the use of a large quantity of chemical substances, resulting in very high costs.

Secondly, it is evident how a waste water and/or digestate purification process requires a significant amount of energy, in particular in the form of thermal energy for heating both the tanks inside which biological treatment is performed and the digesters for treatment of the sludges.

Commonly, as already mentioned, this supply of thermal energy is provided by means of conventional methane gas boilers with the production of hot water.

However, the use of methane gas boilers involves the consumption of huge amounts of fuel.

Therefore, in this sector, research has been concentrated on the provision of alternative systems for the production of thermal energy and, in this connection, it has now become widespread to use biogas boilers, for example boilers which use biogas produced in the aforementioned digesters.

In any case, not all the waste water and/or digestate treatment plants are equipped with digesters along the sludge line, or the latter are unable to provide a sufficient amount of fuel to meet the plant's needs.

Consequently, there is a particularly pressing need to provide an innovative method which is an alternative to those generally used for deodorization of the recycling air containing malodorous substances produced by a purification plant, more specifically a waste water and/or digestate treatment plant.

At the same time, it is desirable to provide a process for the production of thermal energy which is useful for heating the tanks for organic treatment of waste waters and/or for heating the sludge digesters, where provided in the plant, able to overcome the limitations of the solutions described above.

The technical problem forming the basis of the present invention is therefore that of providing a process for deodorization of air containing malodorous substances which is able to limit or avoid entirely the use of chemical substances and at the same allows the production of thermal energy without the further use of boilers specially designed to heat the biological systems of a purification plant.

SUMMARY OF THE INVENTION

This technical problem is solved, according to the present invention, by an innovative process for the thermal abatement of malodorous emissions from a purification plant, with energy recovery from said abatement, the process comprising the steps of:
- feeding a flow of foul air containing malodorous substances emitted from a purification plant, as combustive air into the combustion chamber of a unit for production and recovery of energy, thus producing a flow of high-temperature exhaust gas;
- feeding the aforesaid flow of exhaust gas into a scrubber for the abatement of polluting substances, the aforesaid scrubber using water for the washing of the aforesaid flow of exhaust gas, thus producing a flow of purified gas and a heated washing liquid;
- transferring the aforesaid flow of purified gas to a system for release into the atmosphere, for emission of the aforesaid flow of purified gas into the atmosphere;
- conveying the aforesaid heated washing liquid to a heating jacket of at least one storage tank for the biological treatment of sewage, the aforesaid heating jacket being comprised in the aforesaid purification plant.

Preferably, the aforesaid abatement process further comprises the steps of:
- carrying out an indirect heat exchange between the aforesaid heated washing liquid and the aforesaid sewage, obtaining a cooled washing liquid;
- conveying the aforesaid cooled washing liquid upstream of said purification plant.

Consequently, the process for thermal abatement of malodorous emissions firstly allows advantageously the malodorous substances contained in a flow of foul air from a purification plant to be destroyed by using the same air as combustive air in a combustion chamber of an energy production and recovery unit.

Preferably, the aforesaid energy production and recovery unit uses methane or biogas as a synthesis gas or as fuel.

More specifically, the foul air containing malodorous substances conveyed into the aforesaid combustion chamber not only acts as combustive air, owing to the oxygen naturally present in it, but also helps increase the available heat generated by combustion in the aforesaid chamber.

In fact, the malodorous substances present in the aforesaid foul air, since it is thermally destroyed, contribute to the combustion process, themselves acting as fuel. The aforesaid flow of foul air therefore acts as combustive air, but at the same time may have its own heat value.

Thereafter, the high-temperature exhaust gas thus produced is advantageously cooled and the residual malodorous or polluting substances contained therein are in fact precipitated inside a scrubber so as to produce a flow of cooled and purified discharge gas, which may be easily released into the atmosphere.

Release into the atmosphere may be performed by means of an entirely conventional system for release into the atmosphere, which is preferably included within the aforesaid purification plant.

At the same time, the aforesaid process for the thermal abatement of malodorous emissions is able to provide a heated liquid, more specifically a washing liquid output from the aforesaid scrubber and heated by means of direct heat exchange between the aforesaid flow of high-temperature exhaust gas and the aforesaid washing liquid.

In an equally advantageous manner, the aforesaid heated liquid may be transferred to a system for heating at least one storage tank for the biological treatment of sewage of the aforesaid purification plant and consequently allow the aforesaid sewage to be kept at the desired temperature, preferably without using thermal energy in addition to that produced during the same abatement process.

Preferably, the process for the thermal abatement of malodorous emissions according to the present invention is applied to foul air from a waste water and/or digestate treatment plant. More specifically, in accordance with an embodiment of the present invention, the aforesaid at least one storage tank for the biological treatment of sewage may be a tank for de-nitrification of waste waters or a tank for oxidation/nitrification of waste waters.

In accordance with a further embodiment of the present invention, the aforesaid at least one storage tank for the biological treatment of sewage may be a digester for the anaerobic digestion of the sludges produced in the aforesaid waste water and/or digestate treatment plant.

Preferably, the aforesaid at least one storage tank for the biological treatment of sewage is kept at a temperature comprised between 15° C. and 45° C., and more preferably between 35° C. and 40° C.

In an equally preferable manner, the aforesaid process may comprise feeding the aforesaid scrubber with purified water output from the aforesaid waste water and/or digestate treatment plant, as washing water.

The process according to the present invention may comprise the further steps of:
- transferring a cooled heat-exchange fluid, preferably a diathermic oil, to the aforesaid unit for production and recovery of energy, thus obtaining a flow of heated heat-exchange fluid;
- conveying the aforesaid heated heat-exchange fluid to the heating jacket of at least one sludge drier of the aforesaid purification treatment plant;

carrying out an indirect heat-exchange between the aforesaid heated heat-exchange fluid and the aforesaid sludges, obtaining a cooled heat-exchange fluid and dried sludges.

Therefore, the abatement process according to the present invention may allow heating of a high-temperature heat-exchange liquid and transfer thereof to a drier of a purification plant, such as to allow the drying of wet sludges with consequent production of dried sludges, preferably without using thermal energy in addition to that produced during the same abatement process.

Preferably, in the aforesaid step of transferring the aforesaid heat-exchange fluid to the aforesaid unit for the production and recovery of energy, a heat-exchange fluid heated to a temperature of between 200° C. and 220° C. may be obtained.

Furthermore, in accordance with the process according to the present invention, biogas may be burned inside the aforesaid combustion chamber of the aforesaid unit for the production and recovery of energy.

Preferably, the aforesaid biogas may be generated by a digester for the anaerobic digestion of sludges produced in the aforesaid purification plant.

The aforesaid technical problem is also solved by a system for the thermal abatement of malodorous emissions from a purification plant with energy recovery from said abatement, the system comprising:
- a pipe for collecting foul air containing malodorous substances coming from the aforesaid plant;
- a unit for the production and recovery of energy comprising a combustion chamber in fluid communication with the aforesaid collecting pipe;
- a scrubber for polluting substances in fluid communication with the aforesaid combustion chamber, the aforesaid scrubber being fed with water for the washing of an exhaust gas flow exiting from the aforesaid combustion chamber, the aforesaid scrubber comprising a discharge opening for a washing liquid and a flow conveyor for a purified and cooled exhaust gas flow.
- a distribution header for a washing liquid in fluid communication with said discharge opening, the aforesaid distribution header being in fluid communication with a heating jacket of at least one tank for the biological treatment of sewage of the aforesaid purification plant.

Preferably, the aforesaid flow conveyor for a flow of purified and cooled combustion is in fluid communication with a system for release into the atmosphere, preferably comprised in the aforesaid plant.

The aforementioned technical problem is also solved by a method of revamping a purification plant, wherein the aforesaid plant comprises a system for conveying foul air containing malodorous substances, a deodorizing unit connected to the aforesaid foul air system and a system for release of purified air into the atmosphere connected to the aforesaid deodorizing unit, comprising the steps of:
- providing a collecting pipe and connecting to it the aforesaid system for conveying foul air;
- providing a unit for production and recovery of energy, the aforesaid unit comprising a combustion chamber;
- connecting the aforesaid collecting pipe to the aforesaid combustion chamber;
- providing a scrubber for polluting substances and connecting the aforesaid combustion chamber thereto, wherein the aforesaid scrubber may be fed with water for washing a flow of exhaust gas exiting from the aforesaid combustion chamber, the aforesaid scrubber comprising a discharge opening for a washing liquid and a flow conveyor for a purified and cooled exhaust gas flow;
- providing a distribution header and connecting the aforesaid discharge opening for a washing liquid thereto, the aforesaid distribution header being in fluid communication with a pre-existing heating jacket of at least one tank for the biological treatment of sewage of the aforesaid purification plant.
- connecting the aforesaid flow conveyor to the aforesaid system for releasing purified air into the atmosphere.

Preferably, the aforesaid revamping method according to the present invention is applied to a plant for the treatment of waste waters and/or digestates. In an equally preferable manner the aforesaid revamping method envisages placing the aforesaid scrubber in fluid communication with a pre-existing effluent duct, wherein purified flows out from the aforesaid waste water and/or digestate treatment plant so as to be able to supply the aforesaid scrubber with the aforesaid purified water as washing water.

In an equally preferable manner, the aforesaid revamping method, the aforesaid unit for the production and recovery of energy comprising heating means for an indirect heat exchange between heat-exchange fluid circulating in the aforesaid means and the aforesaid exhaust gas, may comprise further the steps of:
- connecting an entry pipe for conveying the aforesaid heat-exchange fluid to the aforesaid heating means;
- arranging an exit pipe for the transfer of the aforesaid heat-exchange fluid from the aforesaid heating means to the heating jacket of at least one sludge drier of the aforesaid waste water and/or digestate treatment plant and connecting the aforesaid heating means to the aforesaid heating jacket.
- connecting the aforesaid exit pipe to the aforesaid heating jacket of at least one sludge drier of the aforesaid waste water and/or digestate treatment plant.

Further characteristic features and advantages of the present invention will emerge from the description, provided hereinbelow, of a number of preferred examples of embodiment provided by way of a non-limiting example with reference to the accompanying drawings.

DETAILED DESCRIPTION OF A PREFERRED EMBODIMENT

Figure 1:
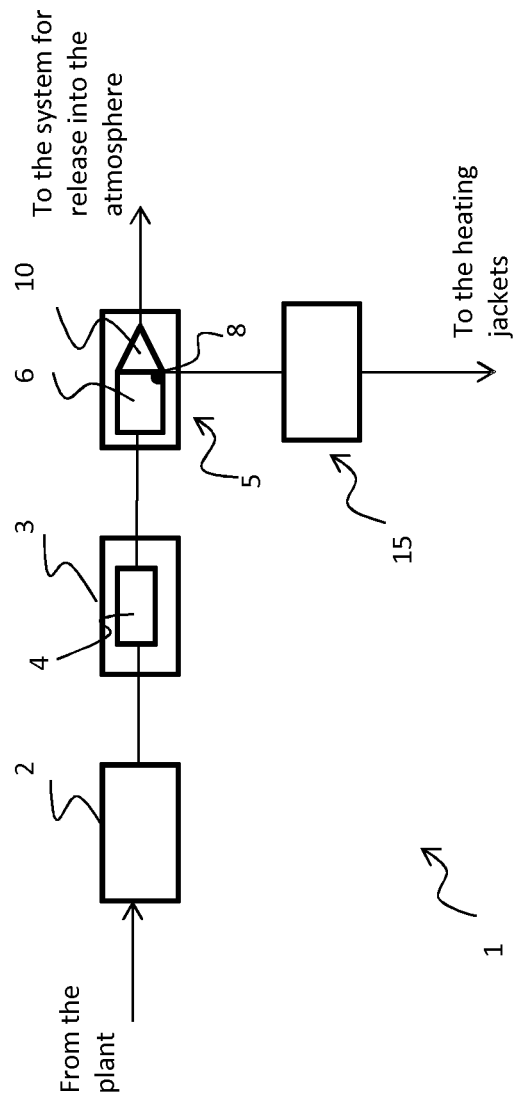
FIG. 1 shows in schematic form a system for the thermal abatement of malodorous emissions from a purification plant with energy recovery from said abatement.

FIG. 1 shows a system 1, indicated overall by 1, for the thermal abatement of malodorous emissions from a purification plant with energy recovery from said abatement, which implements the process according to a mode of implementation of the present invention; this system comprises the following units:

a pipe 2 for collecting foul air containing malodorous substances coming from a purification plant;

a unit 3 for the production and recovery of energy comprising a combustion chamber 4 in fluid communication with the aforesaid collecting pipe 2;

a scrubber 5 for polluting substances in fluid communication with the said combustion chamber, said scrubber 5 is fed with water for washing an exhaust gas flow exiting from the combustion chamber and comprises an abatement chamber 6, a discharge opening 8 for a washing liquid and a flow conveyor 10 for a purified and cooled exhaust gas flow;

a distribution header 15 for a washing liquid in fluid communication with the discharge opening 8 for a washing liquid and with a heating jacket of at least one tank for the biological treatment of sewage of the plant.

Preferably, the flow conveyor 10 for a flow of purified and cooled exhaust gas is connected to and in fluid communication with a system for release into the atmosphere, not shown here because entirely conventional, preferably included in the plant in question.

Preferably the scrubber 5 for polluting substances may be of the type described in European Patent EP 0,749,772 B1.

Figure 2:
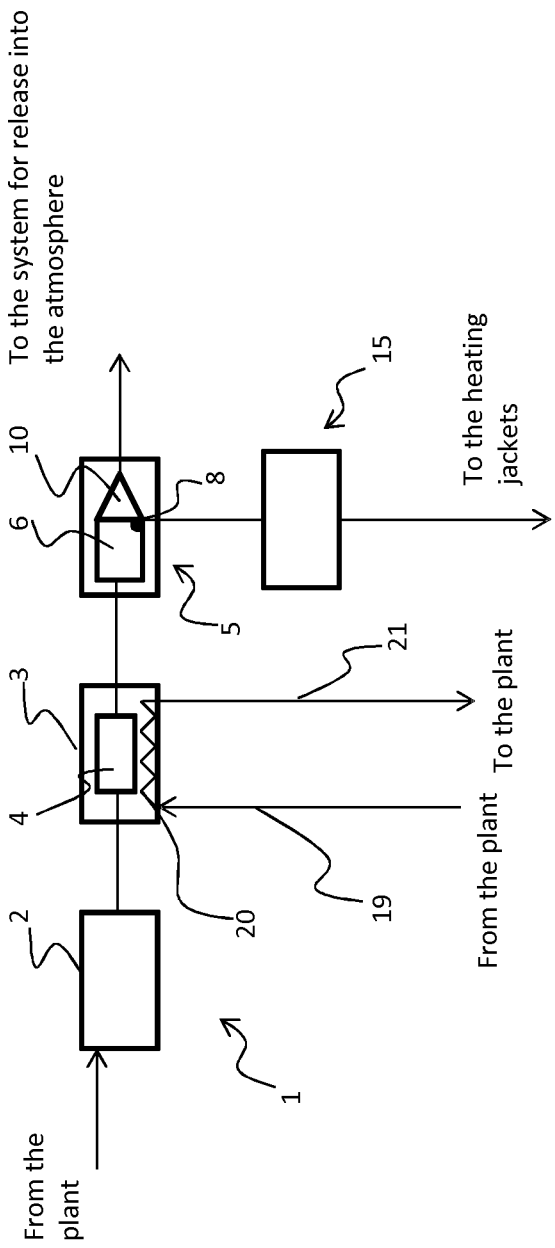
FIG. 2 shows in schematic form a different embodiment of a system for the thermal abatement of malodorous emissions from a purification plant with energy recovery from said abatement.

With reference to FIG. 2, this shows a different embodiment of a system for the thermal abatement of malodorous emissions from a purification plant with energy recovery from said abatement, according to the present invention, which implements a process according to a mode of implementation of the present invention, already described with reference to the summary.

More specifically, in accordance with the aforementioned particular embodiment of a system 1 according to the present invention, the unit 3 for the production and recovery of energy may comprise heating means 20, preferably a heat exchanger, for indirect heat exchange between a heat-exchange fluid circulating in these means and said exhaust gas.

Moreover, the system 1 may further comprise:

an entry pipe 19 intended for conveying a heat-exchange fluid, preferably a diathermic oil, to the heating means 20 and in fluid communication therewith;

an exit pipe 21 for the transfer of the heat-exchange fluid from the heating means 20 to the heating jacket of at least one sludge drier of the purification plant, the exit pipe 21 being in fluid communication with the heating means 20 and with the heating jacket of said sludge drier.

The remaining elements of the system shown in FIG. 2 are structurally and/or functionally equivalent to corresponding elements of the system 1 for thermal abatement of malodorous emissions previously described in FIG. 1 and these elements are attributed the same reference numbers as the latter.

Figure 3:
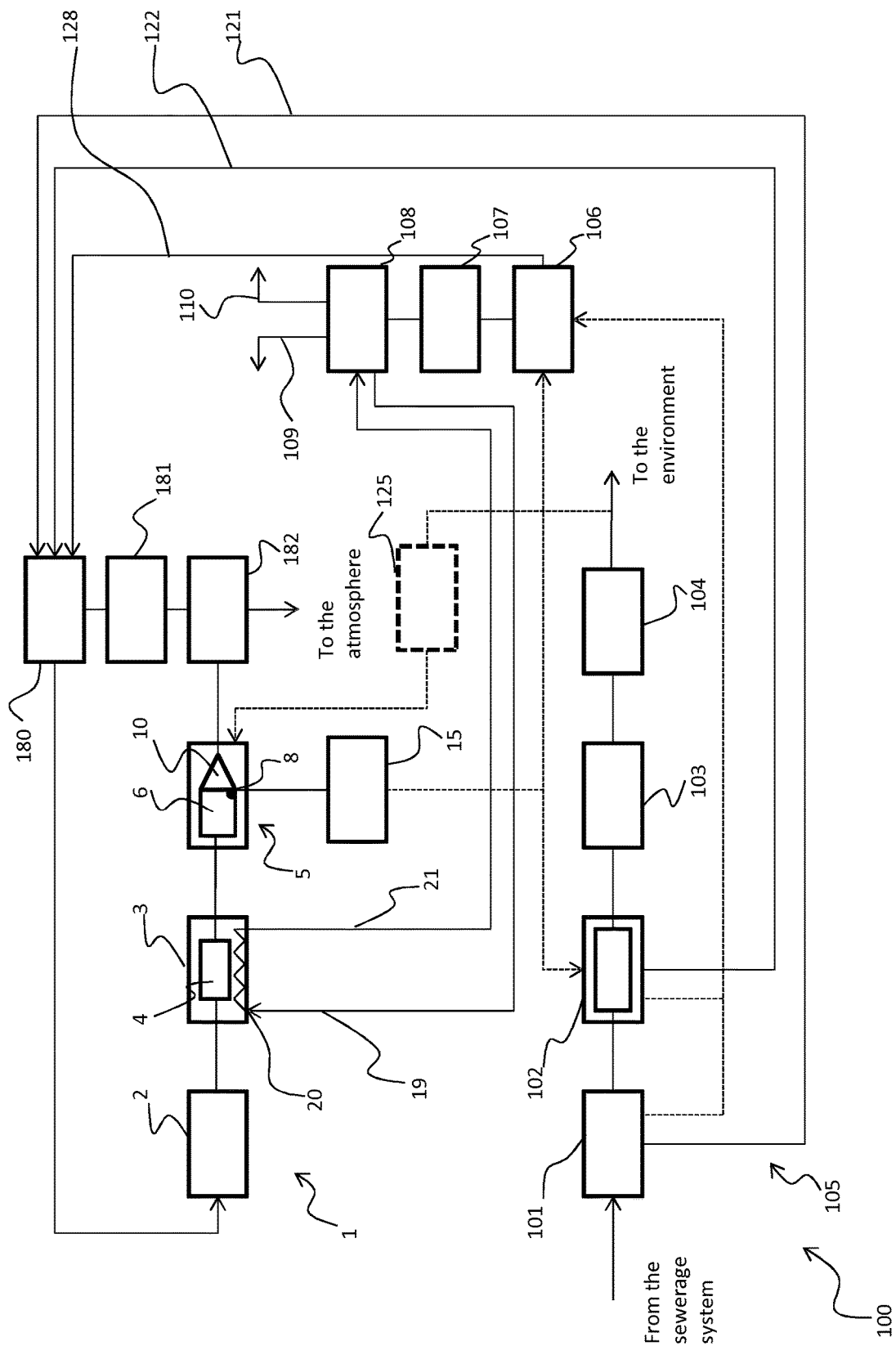
FIG. 3 shows in schematic form a revamped waste water and digestate treatment plant comprising a system for the thermal abatement of malodorous emissions with energy recovery according to the present invention.

With reference to FIG. 3 a plant for the treatment of waste waters and digestates, denoted overall by 100, is described, said plant comprising a system 1 for abatement of malodorous emissions with energy recovery according to the present invention.

The elements of the abovementioned system shown in FIG. 3 are structurally and/or functionally equivalent to corresponding elements of the system for thermal abatement of malodorous emissions previously described in FIG. 2 and these elements are attributed the same reference numbers as the latter.

More specifically, the plant 100 comprises a preliminary treatment zone where the waste waters undergo screening, degritting and oil and grease removal.

A primary duct 121 for foul air connected to a system 180 for conveying the foul air extends from the preliminary treatment zone 101.

Downstream of the preliminary treatment zone there is a biological treatment zone 102 where the pre-treated waste waters undergo a first de-nitrification step and a second oxidation/nitrification step.

The biological treatment zone 102 may comprise at least one tank for biological treatment of sewage, comprising in turn a heating jacket, for maintaining a temperature not higher than 45° C., preferably comprised between 35° C. and 40° C., inside the at least one tank for biological treatment of the sewage.

The at least one tank for biological treatment of sewage which may be included in the zone 102 and said heating jacket are not shown because they are entirely conventional.

A secondary duct 122 for foul air connected to the system 180 for conveying the foul air extends from the preliminary treatment zone 102.

Downstream of the biological treatment zone 102 there is a tertiary treatment zone 103 for sedimentation/settling and filtration of aerated waste waters from the zone 102.

Downstream of the tertiary treatment zone 103 there is located and connected a discharge outlet 104 for releasing the purified waste water into the environment or for transfer thereof to a disinfection zone, not shown since entirely conventional, downstream of which the purified waste water may be reused in the plant or conveyed in an industrial aqueduct for reuse.

A sludge treatment line 105 extends from the biological treatment zone 102 and/or from the tertiary treatment zone 103.

The sludge treatment line 105 comprises a pre-thickening zone 106 in which the density is increased by means of settling and elimination of resultant water which may be transferred into the preliminary treatment zone 101 of the plant 100.

A tertiary duct 128 for foul air connected to the system 180 for conveying the foul air extends from the pre-thickening zone 106.

The sludge treatment line comprises a digestion zone 107, situated downstream of the pre-thickening zone 106, where the thickened sludges undergo an anaerobic digestion step at a temperature typically of between 37° C. to 45° C. for a time period of about 15 to 20 days inside digesters.

The sludge treatment line 105 comprises a dehydration and drying zone 108 situated downstream of the digestion zone 107, where the digested sludges are first dehydrated and then dried. The dehydration and drying zone 108 comprises a drier, not shown since entirely conventional, comprising in turn a heating jacket inside which a diathermic fluid flows.

At the output of the drier there is a line 109 for the vapour condensation and a dried sludge recovery line 110.

The foul air conveying system 180 is connected to and in fluid communication with a collecting pipe 2 included in a system 1 for abatement of malodorous emissions from the plant 100 for treatment of waste waters and digestates with energy recovery from said abatement.

Moreover, the conveyor 10 of the system 1 according to the present invention shown in FIG. 3 is connected to and in fluid communication with a system 182 for release into the atmosphere of purified air from the waste water and digestate treatment plant 100.

At the same time, the discharge opening 8 is connected to and in fluid communication with a distribution header 15 which is in turn connected to the zone 102, more specifically is in fluid communication with the heating jacket of the at least one biological treatment tank comprised therein; the header 15 is also connected to the zone 107, more specifically is in fluid communication with the heating jacket of digester included therein.

The plant 100 is also connected to a pre-existing effluent duct 125 connected to the discharge outlet 104 inside which purified water from the plant flows, so as to be able to supply said scrubber with purified water as washing water.

The plant 100 revamped in accordance with a revamping method according to the present invention further comprises an entry pipe 19 intended for conveying a heat-exchange fluid to the heating means 20 and in fluid communication with said means.

The entry pipe 19 is connected to and is in fluid communication with the heating jacket of the drier included in the dehydrating and drying zone 108.

At the same time, an exit pipe 21 for the transfer of the heated heat-exchange fluid to the heating jacket of this drier for the sludges of the plant is installed downstream of the heating means 20; the exit pipe 21 has the function of placing the heating means 20 in fluid communication with the heating jacket of the drier included in the dehydration and drying zone 108 and allows a heated heat-exchange fluid to be transferred to said jacket The revamped plant 100 described above is effectively realized by means of a revamping method according to the present invention, previously described with reference to the summary of the present invention.

In particular, the revamping method according to the present invention allows the implementation of a system 1 according to the present invention operating in synergy with a pre-existing purification plant, preferably for the treatment of waste waters and digestates, such as that shown in FIG. 3, by making simple modifications thereto.

In particular, as explained in detail further above, it is necessary only to connect the system 180 for conveying the foul air to the collecting pipe 2, connect the distribution header 15 to the cooling jacket of the biological treatment tanks which are to be heated and kept at a suitable temperature with the flow of washing liquid heated by means of the system 1 and, finally, connect the conveyor 10 to a pre-existing system 182 for release into the atmosphere.

With reference to the latter in particular, it should be said that the treatment system 1 is perfectly compatible with a pre-existing system for release of purified air into the atmosphere forming part of a pre-existing purification plant. In fact, the system 1 allows a cooled and purified flow of air to be transferred at temperatures compatible with the materials used to manufacture the pipes of the aforementioned release system, usually plastic material.

Furthermore, the revamping method according to the invention does not envisage necessary decommissioning of the pre-existing deodorizing unit 181 since the latter may be retained as an auxiliary and/or back-up apparatus.

Moreover, the revamped plant 100 described above, comprising a fully operative system 1 according to the present invention, advantageously allows the abatement process to be implemented according to a particular mode of implementation of the present invention.

From the description above it can be seen that the process for the abatement of malodorous emissions according to the present invention solves the technical problem and achieves numerous advantages, the first one being the fact that it is possible to perform effective and practically complete abatement of malodorous substances arising from a flow of foul air from a purification plant.

Since this abatement is performed thermally a large quantity of heat is produced, also owing to the intrinsic heat value of the thus combusted malodorous substances of the foul air, which may be advantageously recycled inside the plant.

At the same time, said abatement is performed by recycling a heated washing liquid as heat-exchange liquid in order to heat and keep at the required temperature the enzymatic treatment tanks of the purification plant in question, which otherwise would have to be heated in a different manner.

Moreover, with the process according to the invention, it is possible to recover further thermal energy produced inside a system for implementing the said process, by means of recycling of a heated heat-exchange fluid, said fluid being transferred to a sludge drier of the purification plant in question.

Therefore, in a particularly innovative and advantageous manner, the present invention provides a single process for the production of thermal energy necessary for operation of the purification plant and for abatement of malodorous emissions.

In addition, in order to reduce further the consumption levels and make the process according to the invention even more sustainable in economic terms, another advantage consists in the possibility of using biogas, optionally produced by the digestion of sludges inside the purification plant, in order to feed the energy production and recovery unit according to the present invention.

Moreover, with a view to saving resources, with the abatement process according to the present invention not only is it possible advantageously to feed a scrubber with purified water output from a waste water and/or digestate treatment plant, instead of with mains water, but also it is possible to transfer, once cooled, the washing water output from the heating jackets of the tanks of the biological treatment plant upstream of a waste water and/or digestate treatment plant where it can be combined with the waste waters and/or digestates to be treated.

In other words, for the same production capacity, the system proposed for implementation of the process according to the present invention is able to ensure operation at lower costs compared to a system needed to obtain this production capacity using the methods of the prior art.

The invention claimed is:

1. A process for the thermal abatement of malodorous emissions from a purification plant with energy recovery from said abatement, said process comprising the steps of:
    feeding a flow of foul air containing malodorous substances emitted from a purification plant, as combustive air into a combustion chamber of a unit for production and recovery of energy, thus producing a flow of exhaust gas;
    feeding said flow of exhaust gas into a scrubber for the abatement of polluting substances, said scrubber using water for the washing of said flow of exhaust gas, thus producing a flow of purified gas and a heated washing liquid;
    transferring said flow of purified gas to a system for release into the atmosphere, for emission of said flow of purified gas into the atmosphere;
    conveying said heated washing liquid to a heating jacket of a storage tank for the biological treatment of sewage, said storage tank being comprised in said purification plant.

2. The process according to claim 1 comprising the further steps of:

carrying out an indirect heat-exchange between said heated washing liquid and said sewage, obtaining a cooled washing liquid;

conveying said cooled washing liquid upstream of said purification plant.

3. The process according to claim 1, wherein said purification plant is a plant for the treatment of waste waters and/or digestates.

4. The process according to claim 3, wherein said storage tank for the biological treatment of waste waters is a tank for de-nitrification of waste waters or a tank for the oxidation/nitrification of waste waters and/or is a digester for anaerobic digestion of the sludges produced in said plant for the treatment of waste waters and/or digestates.

5. The process according to claim 4, wherein said storage tank for the biological treatment of sewage is kept at a temperature comprised between 15° C. and 45° C.

6. The process according to claim 5, wherein said storage tank for the biological treatment of sewage is kept at a temperature comprised between 35° C. and 45° C.

7. The process according to claim 3, wherein said scrubber is fed with purified water, exiting said plant for the treatment of waste waters and/or digestates, as washing water.

8. The process according to claim 1, comprising the further steps of:
   transferring a heat-exchange fluid to said unit for production and recovery of energy, thus obtaining a flow of heated heat-exchange fluid;
   conveying said heated heat-exchange fluid to a sludge dryer of said purification plant;
   carrying out an indirect heat-exchange between said heated heat-exchange fluid and said sludges, obtaining a cooled heat-exchange fluid and dried sludges.

9. The process according to claim 8, wherein said heat-exchange fluid is diathermic oil.

10. A system for the thermal abatement of malodorous emissions from a purification plant with energy recovery from said abatement, said system comprising the following units:
   a pipe for collecting foul air containing malodorous substances coming from said purification plant;
   a unit for the production and recovery of energy comprising a combustion chamber in fluid communication with said collecting pipe;
   a scrubber for polluting substances in fluid communication with said combustion chamber, said scrubber being fed with water for the washing of an exhaust gas flow exiting from said combustion chamber and comprising an abatement chamber, a discharge opening for a washing liquid and a flow conveyor for a purified and cooled exhaust gas flow;
   a distribution header for said washing liquid in fluid communication with said discharge opening, said distribution header being in fluid communication with a heating jacket of at least one tank for the biological treatment of sewage of said purification plant, wherein said unit for the production and recovery of energy comprises heating means for an indirect heat-exchange between a heat-exchange fluid circulating therein and said exhaust gas.

11. The system according to claim 10 comprising the following units:
   an entry pipe for conveying said heat-exchange fluid to said heating means, said entry pipe being in fluid communication with said heating means;
   an exit pipe for the transfer of said heat-exchange fluid from said heating means to the heating jacket of at least one sludge drier of said treatment plant, said exit pipe being in fluid communication with said heating means and with said heating jacket of said sludge drier.

12. A method of revamping a purification plant comprising a system for conveying foul air containing malodorous substances, a deodorizing unit connected to said system for foul air and a system for release of purified air into the atmosphere, which is connected to said deodorizing unit, said method comprising the steps of:
   providing a collecting pipe and connecting it to said system for conveying foul air;
   providing a unit for production and recovery of energy, said unit comprising a combustion chamber;
   connecting said collecting pipe to said combustion chamber;
   providing a scrubber for polluting substances and connecting it to said combustion chamber, said scrubber being fed with water for washing an exhaust gas flow exiting from said combustion chamber, and comprising a discharge opening for a washing liquid and a flow conveyor for a purified and cooled exhaust gas flow;
   providing a distribution header and connecting said discharge opening for a washing liquid thereto, said distribution header being in flow communication with a pre-existing heating jacket of a tank for the biological treatment of sewage of said plant;
   connecting said flow conveyor to said system for release of purified air into the atmosphere.

13. The revamping method according to claim 12, wherein said purification plant is a plant for the treatment of waste waters and/or digestates.

14. The revamping method according to claim 13, wherein said scrubber is connected with a pre-existing effluent duct, in which purified water exiting from said plant for the treatment of waste waters and/or digestates flows, so that said scrubber can be fed with said purified water as washing water.

15. The revamping method according to claim 12, wherein said unit for production and recovery of energy comprises heating means for an indirect heat exchange between a heat-exchange fluid circulating in said means, and said exhaust gas, the method comprising steps of:
   connecting an entry pipe for conveying a heat-exchange fluid, to said heating means;
   arranging an exit pipe for the transfer of said heat-exchange fluid from said heating means to a pre-existing heating jacket of a sludge drier of said purification plant and connecting said heating means to said heating jacket;
   connecting said exit pipe to said heating jacket.

\* \* \* \* \*